United States Patent [19]

Asano et al.

[11] 4,253,302
[45] Mar. 3, 1981

[54] EXHAUST GAS PURIFYING DEVICE FOR INTERNAL COMBUSTION ENGINE

[75] Inventors: Mitsuru Asano; Yoshihiro Segawa, both of Okazaki; Kenji Kondo, Aichi, all of Japan

[73] Assignee: Nippon Soken, Inc., Nishio, Japan

[21] Appl. No.: 922,157

[22] Filed: Jul. 5, 1978

[30] Foreign Application Priority Data

Jul. 8, 1977 [JP] Japan .............................. 52-82107

[51] Int. Cl.³ .............................................. F01N 3/22
[52] U.S. Cl. ................................... 60/276; 204/195 S; 423/213.5
[58] Field of Search .............. 60/276, 301; 204/195 S; 423/213.5; 252/477 R

[56] References Cited

U.S. PATENT DOCUMENTS

| 3,895,917 | 7/1975 | Ravault | 252/477 R |
| 3,951,860 | 4/1976 | Acres | 423/213.5 |
| 3,993,572 | 11/1976 | Hindin | 423/213.5 |
| 4,018,710 | 4/1977 | Oshimura | 423/213.5 |
| 4,038,214 | 7/1977 | Gotoh | 423/213.5 |
| 4,132,615 | 1/1979 | Linder | 204/195 S |
| 4,162,235 | 7/1979 | Acres | 423/213.5 |

FOREIGN PATENT DOCUMENTS 52-39027  3/1977  Japan ............................ 60/276

Primary Examiner—Michael Koczo, Jr.
Attorney, Agent, or Firm—Cushman, Darby & Cushman

[57] ABSTRACT

An oxygen sensor is disposed upstream of a three-way catalyst in an exhaust system of an internal combustion engine and includes a sensing element of metal oxide whose electromotive force or resistance value varies in response to the concentration of oxygen in the engine exhaust gases. A catalytic body including a catalytic metal material exhibiting the same catalytic performance as that of the three-way catalyst is disposed around the sensing element or upstream of the oxygen sensor or is formed by impregnating a portion of the sensing element with the catalytic metal material, so that the air-fuel ratio at the intake side or exhaust side of the engine can be controlled depending on the output of the oxygen sensor.

16 Claims, 10 Drawing Figures

EXHAUST GAS PURIFYING DEVICE FOR INTERNAL COMBUSTION ENGINE

BACKGROUND OF THE INVENTION

This invention relates to an exhaust gas purifying device for an internal combustion engine, in which a three-way catalyst is disposed in the exhaust system of the engine to operate most effectively for purifying the engine exhaust gases by removing toxic components such as CO, HC and NOx contained in the engine exhaust gases. More particularly, this invention relates to an exhaust gas purifying device of the kind above described in which feedback control is applied to the air-fuel ratio at the intake or exhaust side of the engine on the basis of the detected concentration of oxygen in the engine exhaust gases, so that the air-fuel ratio at the intake or exhaust side of the engine can be controlled to permit most effective operation of the three-way catalyst for the purpose of purification of the engine exhaust gases.

An intake control system and an exhaust control system for an internal combustion engine are known in the art. The known intake control system includes a three-way catalyst disposed in the exhaust system of the engine together with an oxygen sensor detecting the concentration of oxygen in the engine exhaust gases, so that the amount of fuel and/or the amount of air at the intake side of the engine can be controlled on the basis of the detected value of the oxygen concentration in the engine exhaust gases. The known exhaust control system controls the air-fuel ratio at the exhaust side of the engine by supplying a suitable amount of secondary air to the exhaust side of the engine (at a point upstream of the three-way catalyst) on the basis of the detected value of the oxygen concentration.

Figure 1:
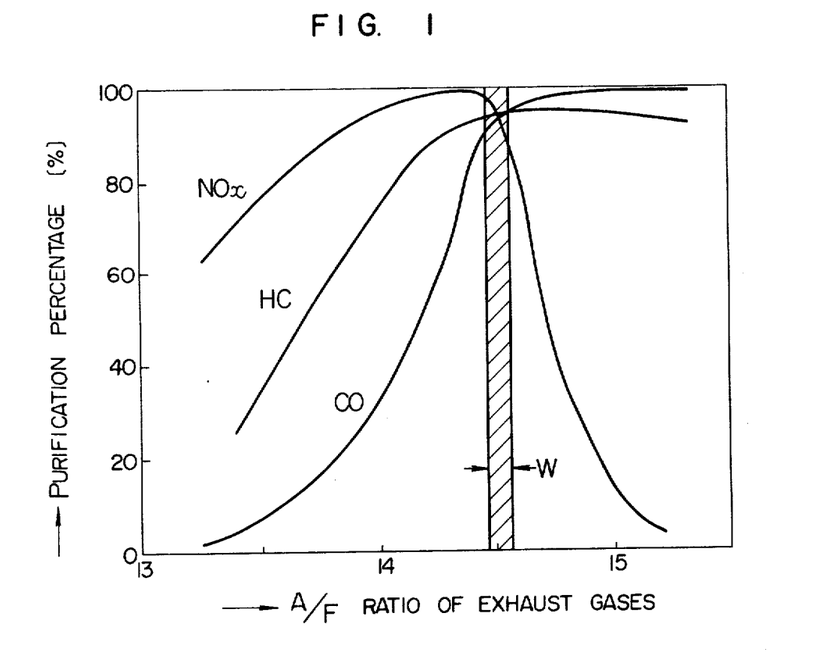
FIGS. 1 and 2 are graphs illustrating the prior art manner of exhaust control.

In order that the three-way catalyst can most effectively operate in these control systems, the air-fuel ratio must be controlled to lie within a narrow region W in FIG. 1 which shows the relation between the air-fuel ratio of engine exhaust gases and the purification percentages of CO, HC and NOx in the engine exhaust gases. This air-fuel ratio region W extends over a narrow width on opposite sides of the stoichiometric air-fuel ratio of the air-fuel mixture (which ratio is set at about 14.5 in the present application), and it is a common practice to employ a sensor sensing the stoichiometric air-fuel ratio of engine exhaust gases and to apply feedback control on the basis of the output of the sensor to make the air-fuel ratio of the engine exhaust gases equal to the stoichiometric one.

Known sensors of this kind include an oxygen sensor utilizing an oxygen ion conductive metal oxide such as zirconium oxide whose output voltage varies in response to the concentration of oxygen in engine exhaust gases, and an oxygen sensor utilizing a metal oxide semiconductor such as titanium oxide whose electrical resistance value varies in response to the concentration of oxygen in engine exhaust gases.

Figure 3:
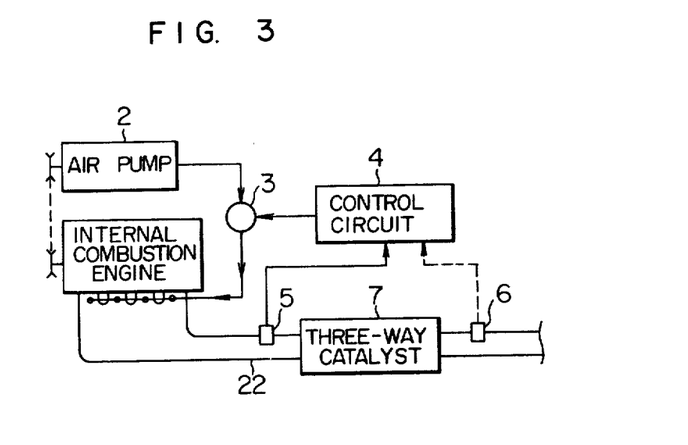
FIG. 3 is a block diagram of an experimental exhaust control system for illustrating the manner of exhaust control according to the prior art and the present invention.

FIG. 3 shows, by way of example, the general arrangement of an exhaust control system in block diagram. The exhaust control system shown in FIG. 3 includes an air pump 2, a solenoid operated valve 3, a control circuit 4, an oxygen sensor 5, and a three-way catalyst 7 for controlling the air-fuel ratio of exhaust gases in an exhaust manifold 22 of an internal combustion engine 1. Such an exhaust control system was used in an experiment conducted by the inventors, with the air pump 2 replaced by factory air, and an additional oxygen sensor 6 disposed downstream of the three-way catalyst 7.

The carburetor is set to provide an air-fuel mixture having an air-fuel ratio of, for example, 13 or 14 which is richer than that of the ideal or stoichiometric air-fuel ratio of 14.5, and the secondary air is supplied in on-off fashion to the engine exhaust gases discharged as a result of combustion of the air-fuel mixture having such a rich air-fuel ratio. The air-fuel ratio of the engine exhaust gases is 13 when no secondary air is supplied to the engine exhaust gases and the carburetor is set to provide the air-fuel mixture having the air-fuel ratio of 13, while the air-fuel ratio of the engine exhaust gases is 16 when the amount of secondary air supplied to the engine exhaust gases is selected to turn the rich air-fuel ratio of 13 into a lean air-fuel ratio of 16. Thus, the rich air-fuel ratio of 13 and the lean air-fuel ratio of 16 are repeatedly provided by the on-off of secondary air supplied to the engine exhaust gases. Therefore, the mean value of the air-fuel ratio of the engine gases is $(13+16)/2=14.5$ which corresponds to the effective operating region of the three-way catalyst, so that the three-way catalyst can most effectively purify the engine exhaust gases. The oxygen sensor 5 is used as the means for the on-off supply of the secondary air. The oxygen sensor 5 has such an operating characteristic that its electromotive force changes abruptly between 0 and 1 volts with the variation of the air-fuel ratio of engine exhaust gases between its rich and lean levels, and this operating characteristic of the oxygen sensor 5 is utilized to actuate the solenoid operated value 3 by the output signal of the oxygen sensor 5 applied through the control circuit 4 thereby attaining the on-off of the secondary air supplied to the engine exhaust gases.

Figure 2:
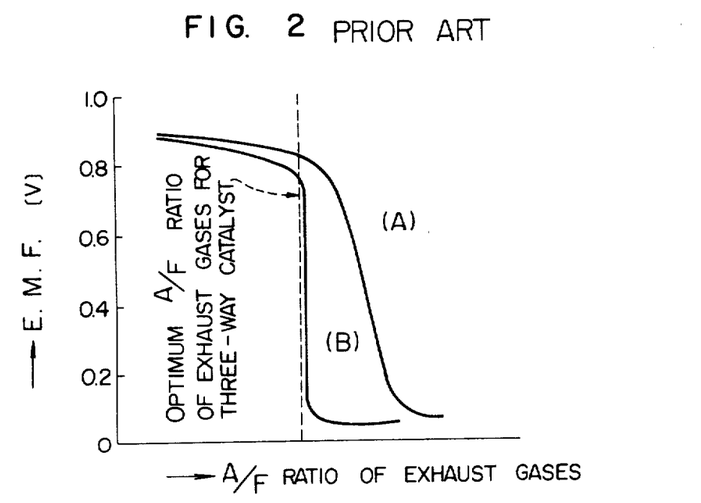

The curve (A) shown in FIG. 2 represents the output of the oxygen sensor 5 in the exhaust control system shown in FIG. 3 when a conventional sensor including a sensing element of zirconium oxide and not having any special catalyst around the sensing element was used as this oxygen sensor 5. It will be seen from FIG. 2 that the electromotive force generated by this oxygen sensor 5 shows a sharp variation in the lean air-fuel ratio range in which the air-fuel ratio is relatively larger than the optimum air-fuel ratio (which is approximately equal to the stoichiometric air-fuel ratio) at which the three-way catalyst 7 operates most effectively. Therefore, in the air-fuel ratio feedback system utilizing such an oxygen sensor, the three-way catalyst cannot operate fully effectively.

As one of means for solving such a problem, the inventors proposed to dispose a metallic catalyst such as platinum (Pt) at a point upstream of the oxygen sensor 5 or around the sensing element of the sensor 5. It was proved that, according to this method, the partial pressure of oxygen in the engine exhaust gases was equilibrated by virtue of the catalytic action of the metallic catalyst, and as a consequence, the electromotive force generated by the oxygen sensor 5 varies only in the vicinity of the optimum air-fuel ratio for the three-way catalyst as shown by the curve (B) in FIG. 2. In this case too, however, the value of the air-fuel ratio did not lie within the desired air-fuel ratio region W shown in FIG. 1 in spite of the purification by the three-way catalyst and deviated toward the right-hand side or leaner side of the desired air-fuel ratio region W. That is, the result of purification was such that the purification percentage of NOx was so low although the purification percentages for CO and HC were satisfactory. In other words, the purification performance of the three-way catalyst was such that the mean air-fuel ratio of the engine exhaust gases obtained as the result of feedback control on the basis of the output of the oxygen sensor was, as it were, controlled to lie on the leaner side of the desired air-fuel ratio region W in FIG. 1.

It will thus be seen that the three-way catalyst cannot still fully effectively operate even when a catalyst, such as, a metallic catalyst, platinum (Pt), different from the three-way catalyst (Pt-Rh) is disposed upstream of the oxygen sensor or around the sensing element of the oxygen sensor.

SUMMARY OF THE INVENTION

It is therefore a primary object of the present invention to provide an improved exhaust gas purifying device for an internal combustion engine, which obviates the defects above described and in which the three-way catalyst disposed in the exhaust system of the engine can operate most effectively.

According to one of the important features of the engine exhaust gas purifying device of the present invention, an oxygen sensor including a sensing element of metal oxide whose electromotive force or electric resistance value varies in response to the concentration of oxygen in engine exhaust gases is disposed in the exhaust system of the engine at a point upstream of a three-way catalyst, and a catalytic body including a catalytic material exhibiting the same catalytic performance as that of the three-way catalyst, or most preferably, the same metallic catalyst as the three-way catalyst, is disposed around the sensing element of the oxygen sensor or at a point upstream of the oxygen sensor, or such a catalytic material is impregnated in a portion of the sensing element of the oxygen sensor as by impregnation means, so that the air-fuel ratio at the intake or exhaust side of the engine can be accurately controlled depending on the output of the oxygen sensor.

The basic concept of the present invention will be described with reference to FIGS. 3 and 4.

Figure 4:
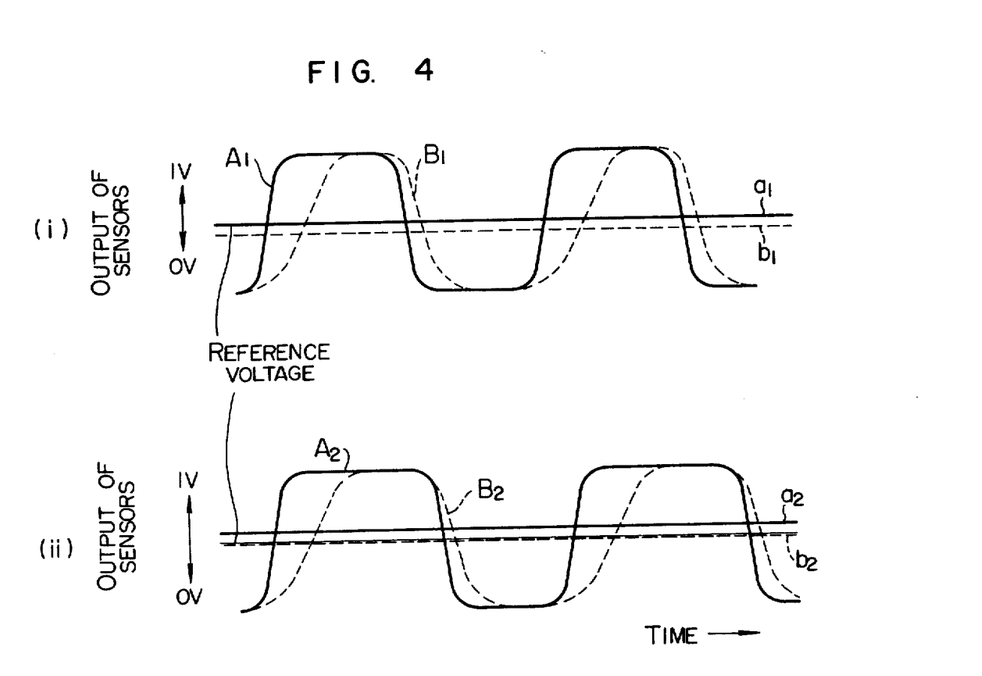
FIGS. 4 are graphs illustrating the output waveforms (i) and (ii) of the oxygen sensors shown in FIG. 3.

FIG. 4 shows the waveforms of outputs of the oxygen sensors 5 and 6 disposed upstream and downstream respectively of the three-way catalyst 7 in the experimental system shown in FIG. 3. The experimental conditions were as follows: The metallic catalyst employed to provide the three-way catalyst 7 was platinum (Pt)-rhodium (Rh). Each of the oxygen sensors 5 and 6 is made of a sensing element of zirconium oxide carrying platinum (Pt) on its outer periphery. The carburetor was adjusted so as to supply an air-fuel mixture having an air-fuel ratio of 13 to the internal combustion engine 1, and the amount of secondary air supplied intermittently into the exhaust manifold 22 by the on-off of the solenoid operated valve 3 was adjusted to provide an air-fuel ratio of 16 at the exhaust side of the engine 1. A hydrocarbon fuel providing a stoichiometric air-fuel ratio (a theoretical air-fuel ratio) of 14.5 was supplied to the engine 1. The control circuit 4 was designed to generate a reference voltage of 0.45 volts to be compared with the electromotive forces generated by the oxygen sensors 5 and 6.

FIG. 4 shows the waveforms (i) of the outputs of the oxygen sensors 5 and 6 when the engine 1 was operated under the above conditions, and the solenoid operated valve 3 was switched on and off in response to the output of the oxygen sensor 5 disposed upstream of the three-way catalyst 7. FIG. 4 shows the waveforms (ii) of the outputs of the oxygen sensors 5 and 6 when the solenoid operated valve 3 was switched on and off in response to the output of the oxygen sensor 6 disposed downstream of the three-way catalyst 7.

From the waveforms (i) in FIG. 4, the inventors discovered the fact that the waveform $A_1$ (shown by the solid lines) of the output of the oxygen sensor 5 disposed upstream of the three-way catalyst 7 differs in its output characteristic from the waveform $B_1$ (shown by the dotted lines) of the output of the oxygen sensor 6 disposed downstream of the three-way catalyst 7, and they investigated the reasons for such a difference between the output waveforms of these sensors.

As a consequence of the investigations, the inventors concluded that the difference between these output waveforms $A_1$ and $B_1$ results from the following factors among others:

(i) The oxygen sensors 5 and 6 are disposed at different locations.
(ii) The engine exhaust gases have different concentrations of oxygen (partial pressures of oxygen) at points upstream and downstream of the three-way catalyst 7 due to the oxidizing and reducing action of the three-way catalyst 7.
(iii) The air-fuel ratios differ at points upstream and downstream of the three-way catalyst 7 due to the oxygen occluding and releasing property (action) of the metallic catalyst forming the three-way catalyst 7.

The inventors considered that the third factor among the three factors enumerated above, that is, the difference between the air-fuel ratios at points upstream and downstream of the three-way catalyst 7 due to the oxygen occluding and releasing action of the three-way catalyst 7 is a most important point for the understanding of the present invention since the present invention is based upon finding of such a difference.

The solid curve $A_1$ in the waveforms (i) of FIG. 4 represents the variation of the air-fuel ratio of the engine exhaust gases flowing into the three-way catalyst 7, and the mean voltage $a_1$ of this solid curve $A_1$ representing the output voltage of the oxygen sensor 5 is approximately equal to the reference voltage of 0.45 volts. Since this means voltage $a_1$ can be regarded to represent the mean air-fuel ratio of the engine exhaust gases flowing into the three-way catalyst 7, and since this mean voltage $a_1$ is approximately equal to the reference voltage, the mean air-fuel ratio of the engine exhaust gases is well controlled to be substantially equal to the value of the stoichiometric air-fuel ratio. In spite of the above fact, the on-off control of the solenoid operated valve 3 in response to the output of the oxygen sensor 5 disposed upstream of the three-way catalyst 7 in the manner shown in the waveforms (i) of FIG. 4 results in such an apparently contradictory phenomenon that a purification performance can only be obtained in which the controlled mean air-fuel ratio lies on the leaner side of the air-fuel ratio region W in FIG. 1. The inventors have, however, found that this phenomenon can be explained or explicated by the oxygen occluding and releasing action of the metallic catalyst. The dotted curve $B_1$ shown in the waveforms (i) of FIG. 4 represents the variation of the air-fuel ratio of the engine exhaust gases flowing out from the three-way catalyst 7, and this air-fuel ratio variation can be said to be the variation of the air-fuel ratio on the active surface of the metallic catalyst forming the three-way catalyst 7. In other words, the air-fuel ratio variation described above can be said to be the variation of the air-fuel ratio of the atmosphere in which the three-way catalyst 7 is actually operating. Such an air-fuel ratio variation is caused on the basis of the fact that the air-fuel ratio of the engine exhaust gases flowing into the three-way catalyst 7 is varied by the oxygen occluding and releasing action of the catalytic metal. This oxygen occluding and releasing action, itself, is described in U.S. Pat. application Ser. No. 863,579 filed on Dec. 22, 1977 and assigned to the same assignee. In this earlier application, a lanthanide oxide such as $CeO_2$ or $LaO_2$ and an n-type semiconductor such as CuO or ZnO are described as a representative of oxygen occluding materials, but platinum (Pt)-rhodium (Rh) itself has also an oxygen occluding and releasing ability. However, due to the fact that the oxygen occluding and releasing ability of Pt-Rh has a certain limit, the lantanide oxides and n-type semiconductors having an oxygen occluding and releasing ability higher than a certain value are disclosed in the earlier application.

As described above, the dotted curve $B_1$ in the waveforms (i) of FIG. 4 represents the variation of the air-fuel ratio of the atmosphere in which the three-way catalyst 7 is actually operating, and such a variation occurs due to the oxygen occluding and releasing action of the catalystic metal Pt-Rh forming the three-way catalyst 7. Therefore, the mean voltage $b_1$ of this dotted curve $B_1$ representing the output voltage of the oxygen sensor 6 can be regarded to be the mean air-fuel ratio of the atmosphere in which the three-way catalyst 7 is actually operating. It is seen from the waveforms (i) of FIG. 4 that this mean voltage $b_1$ is lower than the reference voltage of 0.45 volts. This fact indicates that the mean air-fuel ratio of the atmosphere in which the three-way catalyst 7 is actually operating is controlled at a value which deviates toward the leaner side relative to the stoichiometric air-fuel ratio. Thus, even when the mean air-fuel ratio of the engine exhaust gases flowing into the three-way catalyst 7 is controlled to be set at the stoichiometric air-fuel ratio by means of the feedback control in response to the output voltage of the oxygen sensor 5, the three-way catalyst 7 would not operate most effectively due to the fact that the mean air-fuel ratio of the atmosphere in which the three-way catalyst 7 is actually operating is controlled to take the value at which the mean air-fuel ratio is displaced toward the leaner side of the stoichiometric air-fuel ratio (toward the right relative to the air-fuel ratio region W in FIG. 1) due to the oxygen occluding and releasing action of the catalytic metal. The above fact will be understood from comparison between the curves $A_1$ and $B_1$ in the waveforms (i) of FIG. 4.

On the basis of the above fact and the results of analysis of the fact, the inventors conducted an experiment in an effort to ensure the most effective operation of the three-way catalyst 7. In this experiment, the solenoid operated valve 3 was on-off controlled in response to the output of the oxygen sensor 6 disposed downstream of the three-way catalyst 7, and the air-fuel ratios, that is, the concentrations of oxygen at points upstream and downstream of the three-way catalyst 7 at that time were measured. The solid curve $A_2$ and the dotted curve $B_2$ shown in the waveforms (ii) of FIG. 4 represent the detected waveforms of outputs of the oxygen sensors 5 and 6 disposed upstream and downstream respectively of the three-way catalyst 7.

The solid curve $A_2$ in the waveforms (ii) of FIG. 4 represents the variation of the air-fuel ratio of the engine exhaust gases flowing into the three-way catalyst 7, and the dotted curve $B_2$ represents the variation of the air-fuel ratio of the engine exhaust gases flowing out from the three-way catalyst 7, that is, the variation of the air-fuel ratio of the atmosphere in which the three-way catalyst 7 is actually operating, as in the case of the waveforms (i) of FIG. 4. Also, as in the case of the waveforms (i) of FIG. 4, the mean voltages $a_2$ and $b_2$ of the solid and dotted curves $A_2$ and $B_2$ correspond respectively to the mean air-fuel ratio of the engine exhaust gases flowing into the three-way catalyst 7 and the mean air-fuel ratio of the atmosphere in which the three-way catalyst 7 is actually operating. It will be apparent from the waveforms (ii) of FIG. 4 that the mean voltage $b_2$ is approximately equal to the reference voltage of 0.45 volts, and the mean voltage $a_2$ is slightly higher than the reference voltage. This means that the mean air-fuel ratio of the atmosphere in which the three-way catalyst 7 is actually operating is controlled to be substantially equal to the stoichiometric air-fuel ratio, while the mean air-fuel ratio of the engine exhaust gases flowing into the three-way catalyst 7 is controlled to take the value at which the mean air-fuel ratio is displaced toward the richer side of the stoichiometric air-fuel ratio (toward the left relative to the air-fuel ratio region W in FIG. 1). Therefore, the mean air-fuel ratio of the atmosphere in which the three-way catalyst 7 is actually operating can be controlled to be substantially equal to the stoichiometric air-fuel ratio (the value lying within the air-fuel ratio region W in FIG. 1), so that the three-way catalyst 7 can be operated most effectively.

However, it is generally undesirable to dispose an oxygen sensor at a point downstream of the three-way catalyst 7 for the following reasons: (i) An oxygen sensor cannot properly operate unless its temperature exceeds a certain predetermined level, for example, 300° C. Therefore, during, for example, warming-up of an internal combustion engine, a considerable length of time is required for the temperature of the sensor to reach a temperature above the predetermined level. (ii) The oxygen sensor would not respond satisfactorily, when disposed in such a position, due to an increased delay of system response, since there is a large distance between the position of the sensor 6 and the position of secondary air supply in FIG. 3. (iii) The increased delay of system response results in a correspondingly great variation of the air-fuel ratio, although this point may not pose any particular problem in the case of a system as shown in FIG. 3.

In order to obviate these drawbacks, it is necessary to dispose the oxygen sensor at a point upstream of the three-way catalyst for the feedback control of the air-fuel ratio in response to the output of the sensor. However, the problem described with reference to the waveforms (i) of FIG. 4 cannot be solved when a single oxygen sensor is merely disposed upstream of the three-way catalyst.

In an effort to solve both these two problems, the inventors have made strenuous studies and researches and have found that an engine exhaust gas purifying device is most useful for the desired purposes, in which an oxygen sensor is disposed upstream of the three-way catalyst, and a catalytic body including a catalytic material exhibiting the same catalytic action as that of the catalytic metal forming the three-way catalyst, or more preferably, the same catalytic metal as that forming the three-way catalyst, is disposed upstream of the oxygen sensor or around the sensing element of the oxygen sensor so as to obtain an output voltage similar to that generated by an imaginary oxygen sensor as when such a sensor is disposed downstream of the three-way catalyst. According to such an arrangement, it is possible to detect the air-fuel ratio of the atmosphere substantially the same as that in which the three-way catalyst is actually operating, so that the air-fuel ratio of the atmosphere in which the three-way catalyst is actually operating can be controlled to be substantially equal to the stoichiometric air-fuel ratio thereby ensuring the most effective operation of the three-way catalyst.

DESCRIPTION OF THE PREFERRED EMBODIMENTS

Preferred embodiments of the present invention will now be described in detail with reference to the drawings.

Figure 5:
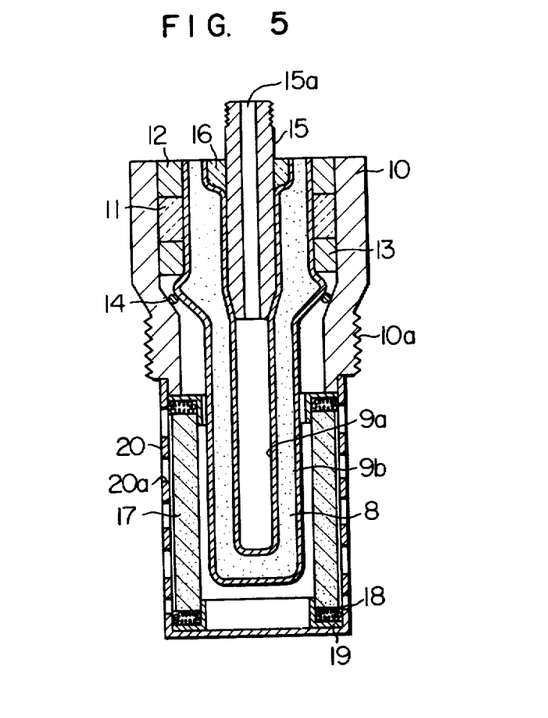
FIG. 5 is a sectional view of an oxygen sensor employed in an embodiment of the exhaust gas purifying device according to the present invention.

Referring first to FIG. 5, the device according to the present invention comprises an oxygen sensor having a structure as shown. The oxygen sensor includes a generally cup-shaped sensing element 8 having an open end and a closed end. This sensing element 8 is formed from an oxygen ion conductive material of solid solution form obtained by sintering the mixture of, for example, zirconium oxide and calcium oxide. A first electrode 9a of platinum and a second electrode 9b of also platinum are deposited on the inner and outer peripheral surfaces respectively of the cup-shaped sensing element 8 by any one of known techniques including vacuum evaporation and paste application. A generally cylindrical housing 10 of metal material having an externally threaded portion 10a surrounds partly the outer periphery of the sensing element 8. An annular member 11 of conductive glass and annular spacers 12, 13 of conductive material are disposed together with an annular washer 14 of conductive material between the cylindrical housing 10 and the cup-shaped sensing element 8 so as to rigidly fix the sensing element 8 to the housing 10. A rod 15 of conductive metal having a central axial bore 15a is fixedly mounted in the opening of the sensing element 8 by means of a layer 16 of conductive glass.

A catalytic body 17 is disposed around the lower part of the sensing element 8. This catalytic body 17 has such a structure that a catalytic metal material, such as Pt-Rh which is the same as that providing the three-way catalyst, is carried by a catalyst carrier such as foamed cordierite or like foamed ceramic or silica cloth which has a high resistance to heat and is permeable to engine exhaust gases. This catalytic body 17 is held against movement by means of a support 18 and a stay 19, and this support 18 is, for example, in the form of a wire net so that vibrations may not be substantially imparted to the catalytic body 17 by being damped by the resiliency of the support 18. A protective tube 20 of heat-resisting and corrosion-resisting metal material having many apertures 20a is fixed to the cylindrical housing 10, and the catalytic body 17 is disposed in the space defined between the protective tube 30 and the cup-shaped sensing element 8. The stay 19 is fixed to the protective tube 20.

Three different catalytic metal materials were used in the catalytic body 17 to provide oxygen sensors Nos. 1 to 3 as shown in Table 1.

TABLE 1

| Catalytic metal | Material of carrier Foamed ceramic |
|---|---|
| Pt | Sensor No. 1 |
| Pt—Rh | Sensor No. 2 |
| Pt—RH—CeO$_2$ | Sensor No. 3 |

EXAMPLE 1

A three-way catalyst of 2.5-liter pellet type having Pt-Rh carried by a carrier of granular γ-alumina was used. (This pellet type three-way catalyst is commonly known in the art, and the carrier is contained in a container.) This three-way catalyst and the oxygen sensor No. 2 shown in Table 1 were disposed at the positions 7 and 5 respectively in FIG. 3, and the oxygen sensor No. 2 was operated under the following conditions to measure the purification performance of the exhaust control system:

Internal combustion engine:
 6-cylinder, 4-cycle, 2,000 cc engine
Revolution and suction vacuum:
 2,000 rpm, −240 mm Hg
Secondary air supply:
 Factory air was supplied in on-off fashion to the exhaust manifold by the solenoid operated valve in response to the output of the oxygen sensor disposed upstream of the three-way catalyst.
Air-fuel ratio:
 13.0 in the "off" state of secondary air (the air-fuel ratio at the engine intake side)
 16.0 in the "on" state of secondary air (the air-fuel ratio at the engine exhaust side)
Sensor control voltage: 0.45 volts

EXAMPLE 2

The oxygen sensor No. 3 was used in conjunction with a three-way catalyst of 2.5-liter pellet type having Pt-Rh-CeO$_2$ carried by a γ-alumina carrier, and the purification performance was measured under the same conditions as those in EXAMPLE 1.

EXAMPLE 3

The foamed ceramic used as the catalyst carrier in the catalytic body 17 in the oxygen No. 2 employed in EXAMPLE 1 was replaced by a silica cloth formed by weaving high-purity silica (SiO$_2$) fibers and carrying Pt-Rh, and the purification performance was measured under the same conditions as those in EXAMPLE 1.

COMPARATIVE EXAMPLE 1

The oxygen sensor shown in FIG. 5 but not provided with the catalytic body 17 was used, and the purification performance was measured under the same conditions as those in EXAMPLE 1.

COMPARATIVE EXAMPLE 2

The oxygen sensor No. 1 was used, and the purification performance was measured under the same conditions as those in EXAMPLE 1.

Table 2 shows the results of measurement of purification percentages for CO, HC and NOx in EXAMPLES 1 to 3 and COMPARATIVE EXAMPLES 1 and 2.

TABLE 2

| Purification percentage Example | Purification percentage | | |
|---|---|---|---|
| | CO | HC | NOx |
| EXAMPLE 1 | 91.2 | 99.0 | 90.2 |
| EXAMPLE 2 | 93.0 | 98.5 | 92.0 |
| EXAMPLE 3 | 90.5 | 97.0 | 91.2 |
| COMPARATIVE 1 | 95.0 | 98.7 | 34.0 |
| COMPARATIVE 2 | 96.0 | 99.5 | 72.5 |

Figure 6:
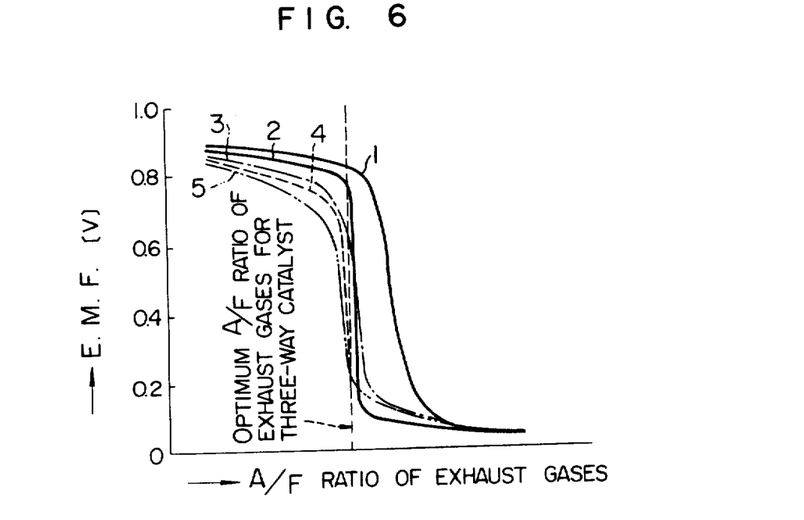
FIG. 6 is a graph illustrating the manner of exhaust control according to the present invention.

FIG. 6 shows the variation of the outputs of the oxygen sensors in the five examples above described relative to the variation of the air-fuel ratio of engine exhaust gases, that is, the variation of the sensor outputs when the air-fuel ratio of engine exhaust gases is gradually varied from the richer side toward the leaner side.

It will be seen from Table 2 that COMPARATIVE EXAMPLES 1 and 2 show lower purification percentages for NOx than EXAMPLES 1 to 3, but show relatively higher purification percentages for CO and HC than EXAMPLES 1 to 3. COMPARATIVE EXAMPLES 1 and 2 show such results due to the fact that the air-fuel ratio of the engine exhaust gases flowing into the three-way catalyst and/or the air-fuel ratio of the atmosphere in which the three-way catalyst is actually operating are displaced toward the leaner side relative to the air-fuel ratio region W in FIG. 1. One of the reasons is attributable to the fact that the abrupt varying position of the output of the oxygen sensor deviates from the air-fuel ratio region W as will be apparent from the curve 1 in FIG. 6 representing the output of the oxygen sensor employed in COMPARATIVE EXAMPLE 1. Thus, this oxygen sensor does not primarily perform the oxygen sensing function. Although the curve 2 representing the output of the oxygen sensor employed in COMPARATIVE EXAMPLE 2 is relatively analogous to the curves 3, 4 and 5 representing the sensor outputs in EXAMPLES 1 to 3, this oxygen sensor is not acceptable as the purification percentage for NOx is so low. As explained hereinbefore, this is attributable to the fact that the mean air-fuel ratio of the atmosphere in which the three-way catalyst is actually operating is controlled to take a value which is displaced toward the leaner side relative to the stoichiometric air-fuel ratio.

It will be seen from Table 2 that all the purification percentages for the exhaust gas components are higher than 90% in EXAMPLES 1 to 3, and this proves that the three-way catalyst is properly or most effectively operating. That is, the three-way catalyst operates in the atmosphere in which the air-fuel ratio lies within the air-fuel ratio region W shown in FIG. 1.

It will thus be seen that, for the most effective operation of the three-way catalyst, a catalytic metal material having the same catalytic performance as that of the three-way catalyst should be disposed upstream of the oxygen sensor or around the sensing element of the oxygen sensor.

Figure 7:
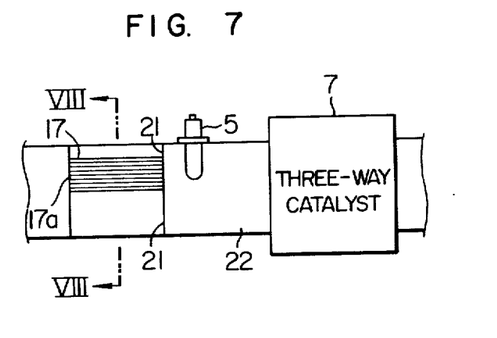
FIG. 7 is a schematic sectional view of part of another embodiment of the present invention.
Figure 8:
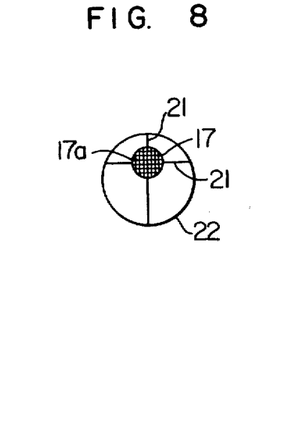
FIG. 8 is a sectional view taken on the line VIII—VIII in FIG. 7.

FIGS. 7 and 8 show part of a modification of the exhaust gas purifying device of the present invention, in which the catalytic body 17 is disposed upstream of the oxygen sensor 5 instead of being disposed around the sensing element 8 of the oxygen sensor 5. In this modification, the catalytic body 17 is composed of a monolithic carrier of cordierite having many axial passages 17a, and a catalytic metal material carried in these passages 17a. This catalytic body 17 is fixedly held in position within the exhaust manifold 22 by means of a fully resilient stay 21.

In another modification of the present invention, a porous coating of material such as γ-alumina may be deposited on the outer surface of the second electrode 9b exposed to the engine exhaust gases in the sensing element 8 of the oxygen sensor shown in FIG. 5, and a catalytic metal material may be carried on such a coating to provide the catalytic body 17.

Figure 9A:
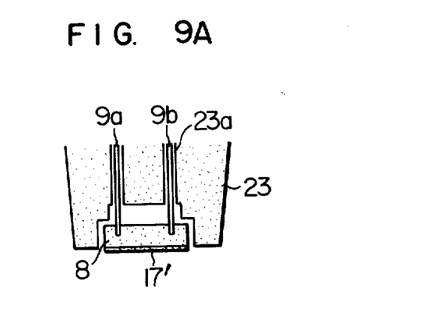
FIGS. 9A and 9B are schematic sectional views of part of other forms of the oxygen sensor employed in the device according to the present invention.
Figure 9B:
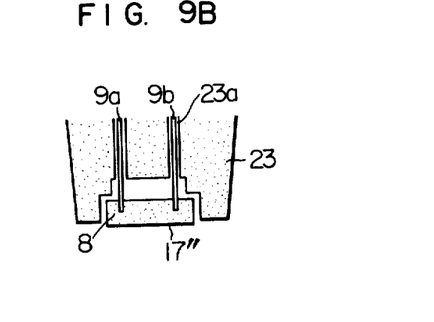

FIGS. 9A and 9B show part of other forms of the oxygen sensor preferably employed in the present invention, in which the sensing element 8 is formed from a metal oxide such as titanium oxide. In the oxygen sensor shown in FIG. 9A, a catalytic body 17' of, for example, Pt-Rh is directly provided on the bottom of the sensing element 8, while in the oxygen sensor shown in FIG. 9B, a catalytic body 17'' is provided as by directly impregnating a portion of the sensing element 8 with a catalytic metal material such as Pt-Rh. In FIGS. 9A and 9B, the two electrodes 9a and 9b are each in the form of an electrode rod extending into the sensing element 8 without being electrically shorted by the catalytic body 17' or 17''. In each case, the sensing element 8 is held in an alumina or like insulator 23 provided with a pair of spaced bores 23a to permit insertion of the electrodes 9a and 9b therein.

The present invention is also applicable to an exhaust gas purifying device which controls the amount of intake air or fuel supplied to an internal combustion engine thereby controlling the air-fuel ratio of the air-fuel mixture at the intake side of the engine.

The three-way catalyst is in no way limited to the pellet type and may be of the monolithic type including a monolithic carrier of, for example, cordierite having many axial passages for holding a catalytic material therein.

The cylindrical sensing element of zirconium oxide constituting part of the oxygen sensor may be replaced by a planar one.

The catalytic body combined with the sensing element of the oxygen sensor need not necessarily be formed from the same catalytic metal material as that forming the three-way catalyst. When, for example, a metal oxide capable of simultaneously removing CO, HC and NOx in engine exhaust gases is used to form the three-way catalyst, the catalytic body may be formed from a catalytic metal material exhibiting the same catalytic performance as that of the metal oxide.

We claim:

1. An exhaust gas purifying device for an internal combustion engine comprising a three-way catalyst disposed in the exhaust system of the engine, an oxygen sensor disposed upstream of said three-way catalyst in said exhaust system and including a sensing element generating an output signal varying in response to the concentration of oxygen in the engine exhaust gases, and means for controlling the air-fuel ratio at the intake side or exhaust side of the engine depending on the output signal of said oxygen sensor, wherein the improvement comprises another three-way catalyst disposed in the vicinity of said sensing element to produce around said sensing element an exhaust gas atmosphere which is substantially the same as the atmosphere in which said three-way catalyst is actually operating.

2. An exhaust gas purifying device as claimed in claim 1, wherein said another three-way catalyst is disposed around said sensing element.

3. An exhaust gas purifying device as claimed in claim 1, wherein said another three-way catalyst is disposed upstream of said sensing element in said exhaust system.

4. An exhaust gas purifying device as claimed in claim 1, wherein said another three-way catalyst is formed by impregnating a portion of said sensing element with a catalytic material.

5. An exhaust gas purifying device as claimed in claim 1 or 2, wherein said another three-way catalyst is substantially the same as that of said three-way catalyst.

6. An exhaust gas purifying device as claimed in claim 1 or 2, wherein both said three-way catalysts include Pt-Rh.

7. An exhaust gas purifying device as claimed in claim 1 or 2, wherein both said three-way catalysts include Pt-Rh-CeO$_2$.

8. An exhaust gas purifying device as claimed in claim 1 or 2, further including means for carrying said another three-way catalyst, said carrying means being permeable to engine exhaust gases.

9. An exhaust gas purifying device as claimed in claim 8, wherein said carrier means is a foamed ceramic.

10. An exhaust gas purifying device as claimed in claim 8, wherein said carrier means is a silica cloth.

11. An exhaust gas purifying device for an internal combustion engine comprising a three-way catalyst disposed in the exhaust system of the engine, an oxygen sensor disposed upstream of said three-way catalyst in said exhaust system and including a sensing element generating an output signal varying in response to the concentration of oxygen in the engine exhaust gases, and means for controlling the air-fuel ratio at the intake side or exhaust side of the engine depending on the output signal of said oxygen sensor, wherein the improvement comprises another three-way catalyst in the vicinity of said sensing element to produce around said sensing element an exhaust gas atmosphere substantially the same as that produced by said three-way catalyst.

12. An exhaust gas purifying device as claimed in claim 11, wherein said another three-way catalyst is formed by impregnating a portion of said sensing element serving as said catalyst carrier means with a catalytic material.

13. An exhaust gas purifying device as claimed in claim 11 or 12, wherein said another three-way catalyst is the same as said three-way catalyst.

14. An exhaust gas purifying device as claimed in claim 11 or 12, wherein both said three-way catalysts include Pt-Rh.

15. An exhaust gas purifying device as claimed in claim 11 or 12 wherein both said three catalysts include Pt-Rh-CeO$_2$.

16. An exhaust gas purifying device as claimed in claim 11 or 12 wherein said catalyst carrier means is made of material permeable to the engine exhaust gases.

* * * * *